Figure 1:
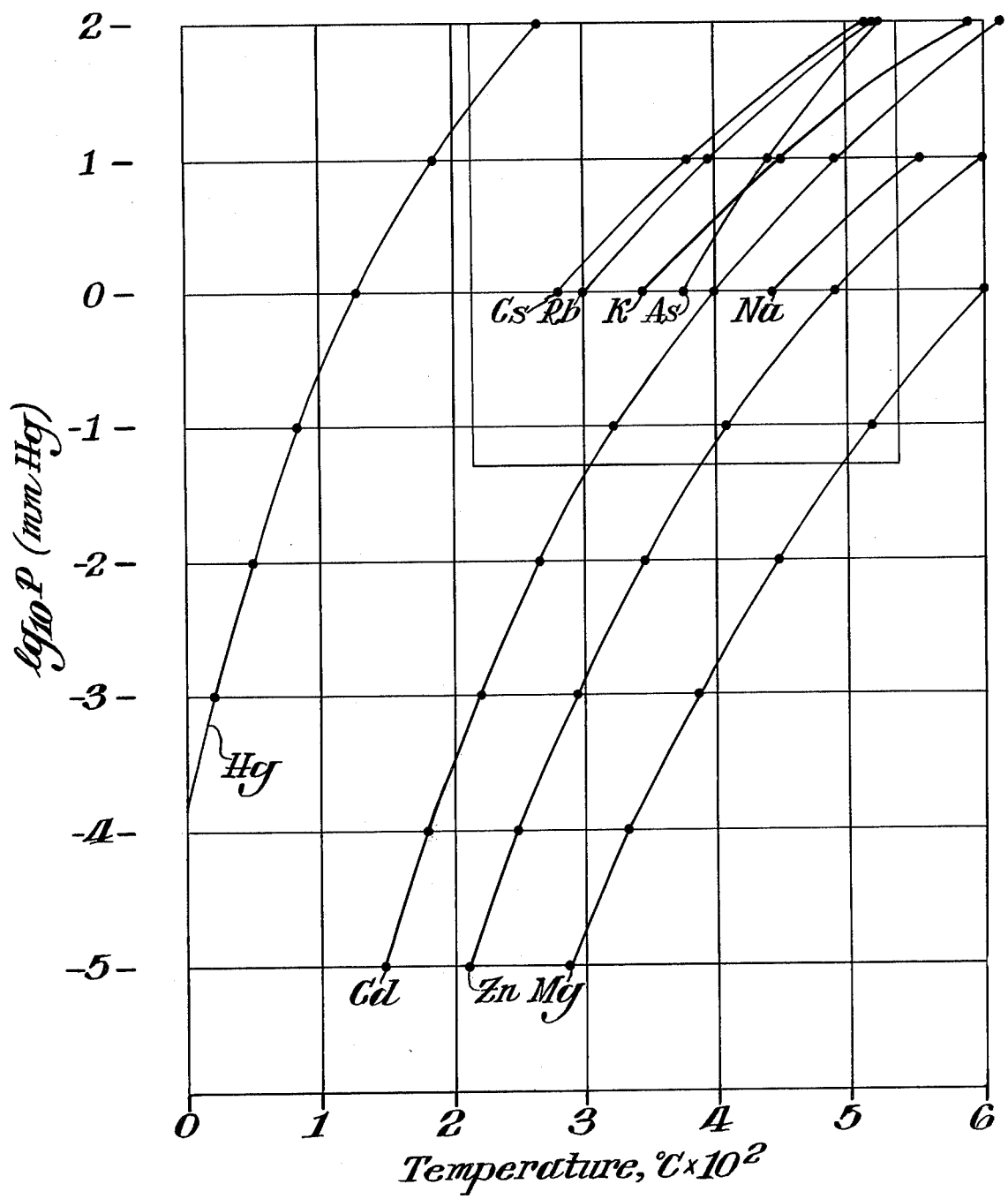

United States Patent [19]

Fraenkel et al.

[11] 4,294,725

[45] Oct. 13, 1981

[54] CATALYST, METHOD FOR CATALYST MANUFACTURE AND USE

[75] Inventors: Dan Fraenkel; Bruce C. Gates, both of Newark, Del.

[73] Assignee: University of Delaware, Newark, Del.

[21] Appl. No.: 95,989

[22] Filed: Nov. 20, 1979

[51] Int. Cl.$^3$ .............................................. B01J 29/14
[52] U.S. Cl. ................................. 252/455 Z; 518/715
[58] Field of Search ............. 252/455 Z; 260/449.6 R

[56] References Cited

U.S. PATENT DOCUMENTS

| | | | |
|---|---|---|---|
| 3,013,983 | 12/1961 | Breck et al. | 252/455 Z |
| 3,013,984 | 12/1961 | Breck | 252/455 Z |
| 3,013,987 | 12/1961 | Castor et al. | 252/455 Z |
| 3,013,990 | 12/1961 | Breck et al. | 252/455 Z |
| 3,200,082 | 8/1965 | Breck et al. | 252/455 Z |
| 4,139,550 | 2/1979 | Seitzer | 260/449.6 R |
| 4,199,522 | 4/1980 | Murchison et al. | 260/449.6 R |
| 4,207,248 | 6/1980 | Butter et al. | 260/449.6 R |

OTHER PUBLICATIONS

Carbon Monoxide-Hydrogen Reactions—Kirk-Othmer "Encyclopedia of Chem. Tech.", Wiley Co., 2nd Ed., vol. 4, 1964, pp. 446–489.

Chain Limitation of Fischer-Tropsch Products in Zeolites, Hubert H. Nijs et al., J.C.S. Chem. Comm., 1979, pp. 180–181.

The Fischer-Tropsch Reaction, Masters and Fraenkel, Academic Press, 1979, pp. 61–102.

*Primary Examiner*—Carl F. Dees

[57] ABSTRACT

A Fischer-Tropsch catalyst comprising a particulate synthetic zeolite incorporating a transition metal catalyst reduced in situ by a preselected vaporous reductant metal, the method of catalytic manufacture and use.

3 Claims, 5 Drawing Figures

CATALYST, METHOD FOR CATALYST MANUFACTURE AND USE

The Government of the United States has certain rights to this invention pursuant to National Science Foundation Grant No. ENG-7826054.

INTRODUCTION

This invention relates to a highly selective catalyst giving improved yields in the conversion of carbon monoxide and hydrogen. For classification purposes, our catalyst can be considered to be a Fischer-Tropsch type.

BACKGROUND OF THE INVENTION

There presently exist a number of Fischer-Tropsch catalysts, including at least one commercial type employing Co:ThO$_2$ deposited on kieselguhr, all as described by H. Pichler and A. Hector in the *Encyclopedia of Chemical Technology, Kirk-Othmer*, vol. 4, pp. 446–489, Interscience Publishing Company (1964). Generally, these catalyst produce a mixture of hydrocarbon products which require subsequent separation, which is expensive. In addition, some of the products have no ready markets at the time of production, thereby constituting an economic disadvantage (refer Catalysis Reviews-Sci. Eng. 14 (2) pp. 153–191 (1976) by M. A. Vannice). Moreover, the product yields of known Fischer-Tropsch catalysts are less than optimum.

OBJECT OF THE INVENTION

An object of this invention is the provision of an improved Fischer-Tropsch catalyst of high performance, improved specificity of product manufacture and economical in first cost and long term use.

SUMMARY OF THE INVENTION

Generally, this invention comprises a Fischer-Tropsch catalyst constituting a preselected microporous support, e.g., a synthetic zeolite within which a preselected transition metal, such as, for example, Co, is exchanged, after which the transition metal is reduced by the vapor of a preselected metal having an appreciable electromotive series potential difference from the transition metal, e.g., Cd, where Co is the specific transition metal supra. Depending upon the transition metal, reductant metal choice, and the particular synthetic zeolite employed as the catalyst support, it is possible to obtain an exceedingly high product selectively (specificity), high production rate of a given product, e.g., (1) propylene, in the case of a zeolite 5A (Ca-A) support, which has undergone ion exchange with a cobalt salt followed by reduction with Cd in the vapor phase or (2) a mixture of C$_4$–C$_7$ hydrocarbons in the case of a zeolite of the Faujasite family which has undergone ion exchange with a cobalt salt followed by reduction with Cd in the vapor phase.

DRAWINGS

Figure 2A:
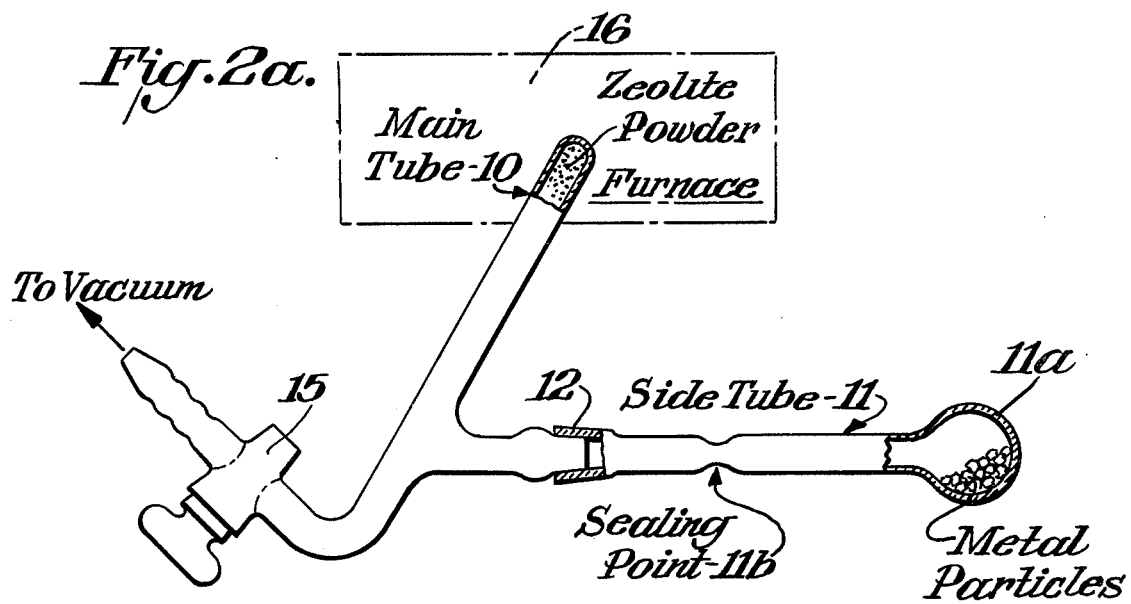
Figure 2C:
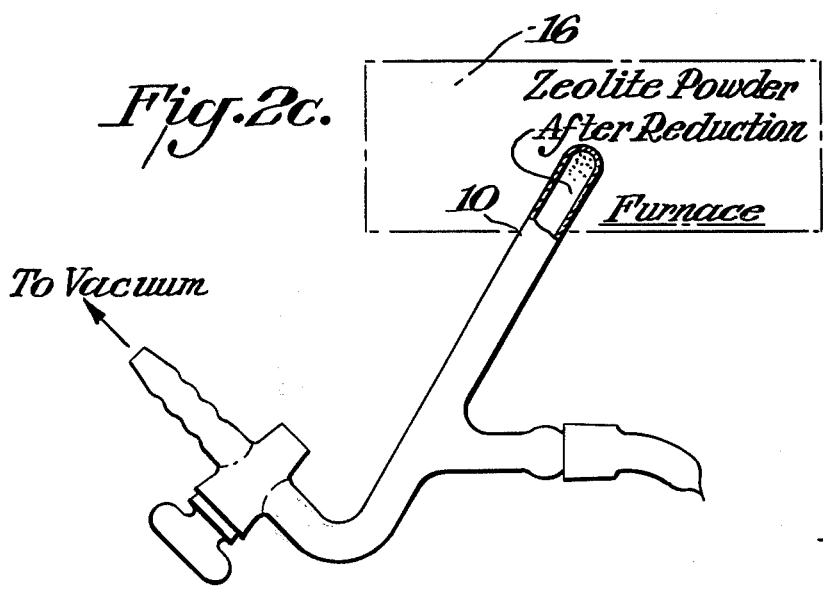
Figure 2B:
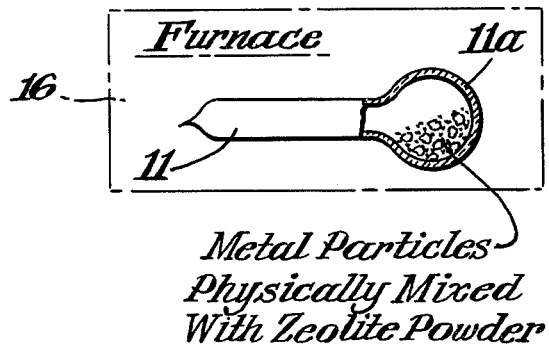
Figure 3:
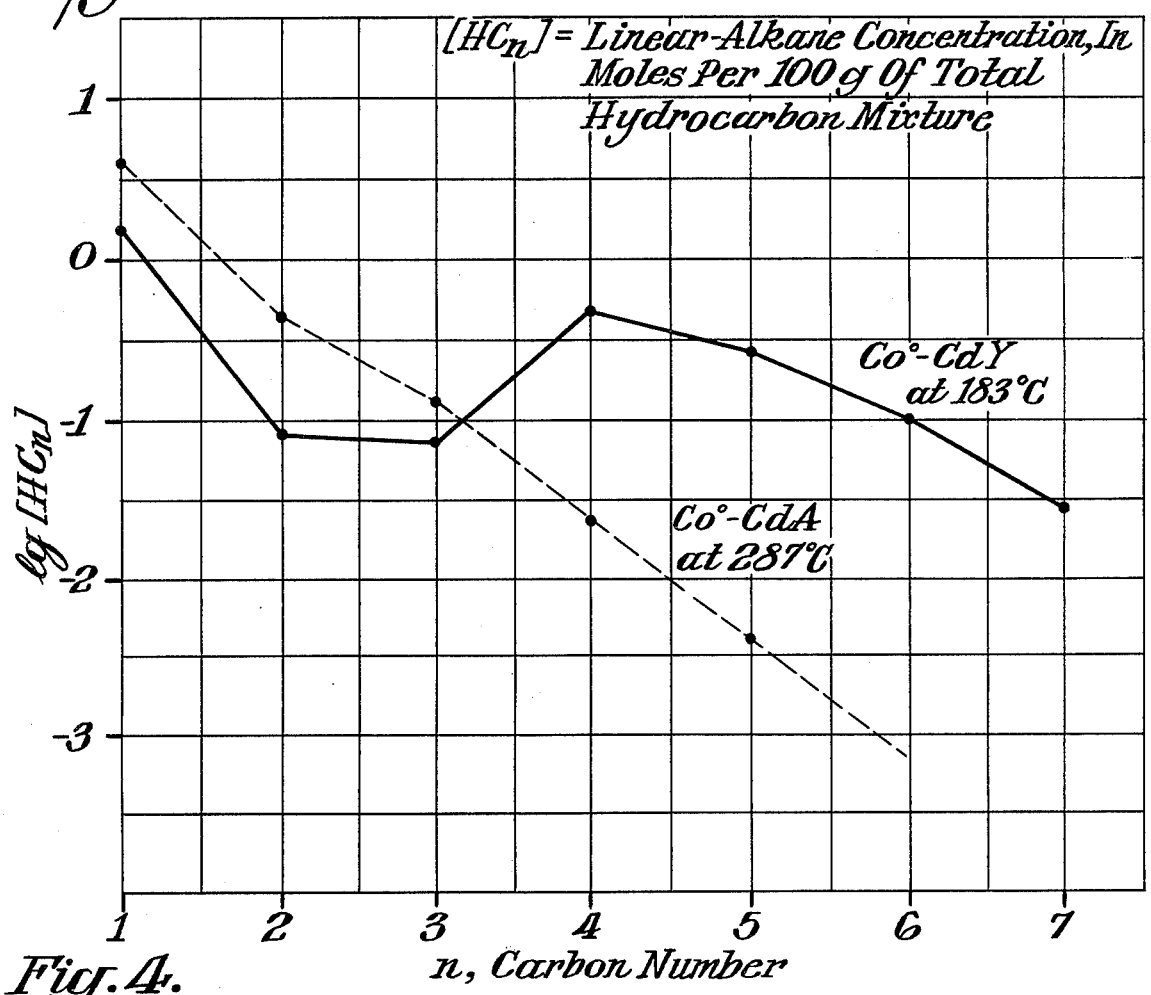
Figure 4:
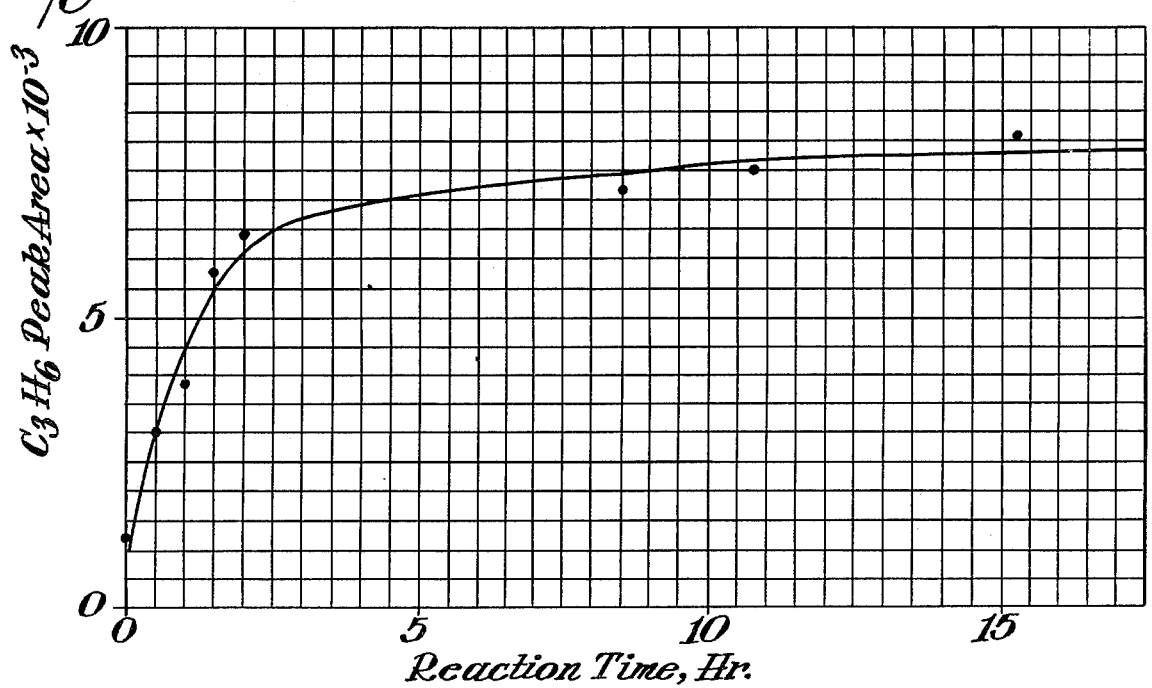
Figure 5:
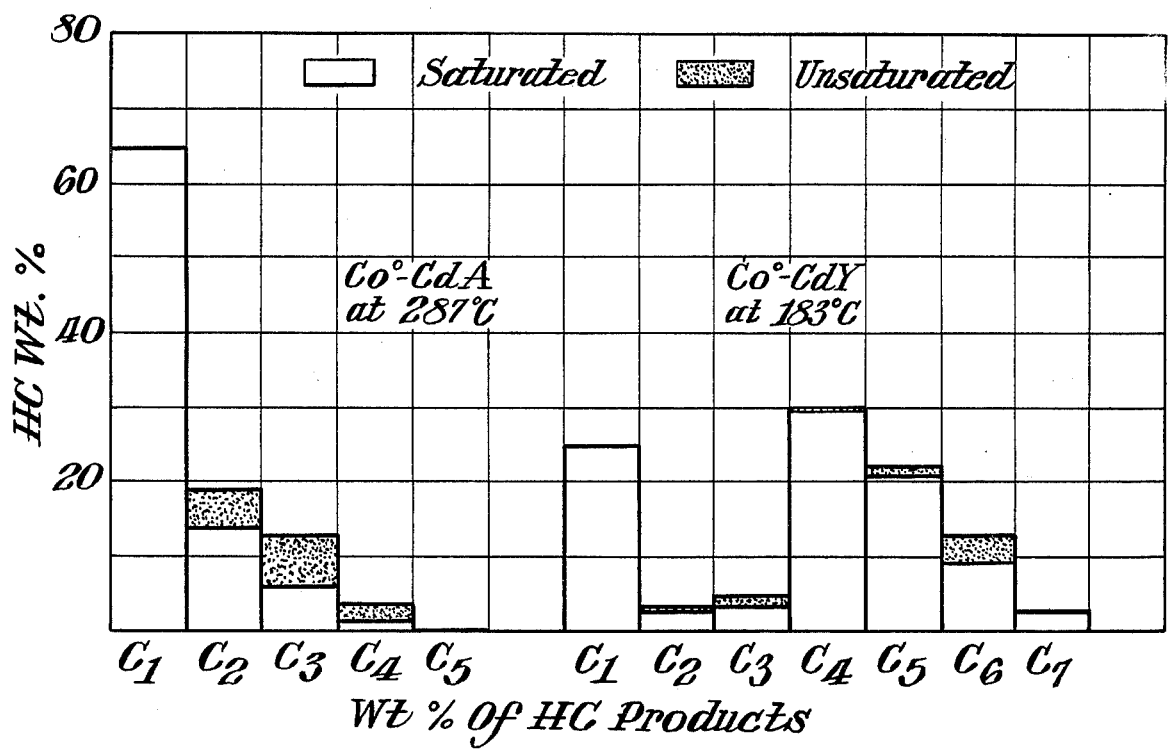

The following drawings constitute part of this disclosure, in which:

FIG. 1 is a schematic portrayal of transition metals, log partial pressures, mm Hg v. temperature, °C.×10$^2$ as an aid in catalyst selection according to this invention, FIG. 2 overall is a schematic representation of laboratory apparatus utilized in the manufacture of a preferred Co transition metal, Cd reducing metal, incorporated in a synthetic zeolite type catalyst according to this invention in which FIG. 2a shows the first stage activation apparatus, FIG. 2b shows the sealed tube detached from FIG. 2a apparatus, as employed for the second stage reduction, and FIG. 2c shows the apparatus remainder after the reductions of FIGS. 2a and 2b as employed for the third stage removal of excess metallic reductant, FIG. 3 is a plot of log [HC$_n$] v. n, Number of Carbons in Hydrocarbon Products for catalyst Co°-CdA and Co°-CdY, respectively, FIG. 4 is a plot of C$_3$H$_6$ Peak Area×10$^{-3}$ v. Reaction Time, Hrs. for Experiment #2 F-T, and FIG. 5 is a comparison plot of Hydrocarbons, Wt. Percent v. Weight Percent of Hydrocarbon Products for (1) Co°-CdA at 287° C. and (2) Co°-CdY at 183° C.

DESCRIPTION OF THE INVENTION

The various types and properties of synthetic zeolites, except their uses in catalysis (which subject was deliberately omitted by the author, refer Preface, page v) are described extensively in the book *Zeolite Molecular Sieves, Structure, Chemistry and Use*, by Donald W. Breck, John Wiley & Sons (1974).

According to Breck, supra, the structural formula of a zeolite is best expressed for the crystallographic unit cell as

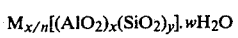

$$M_{x/n}[(AlO_2)_x(SiO_2)_y] \cdot wH_2O$$

where
  M = the cation of valence n,
  w = the number of water molecules, and the ratio y/x usually has values of 1–5, depending upon the structure. The sum (x+y) is the total number of SiO$_4$ plus AlO$_4$ tetrahedra in the unit cell. The portion within [0] represents the framework composition.

Table 4.26 "Alphabetical List of Synthetic Zeolites" of Breck pp. 348–52 supra tabulates an alphabetical list of synthetic zeolites, together with major properties, including, particularity, cations, structural stability toward dehydration, pore size, pore volume, framework in terms of principal constituents, such as Si/Al ratios, and X-ray data.

An important advantage of the molecular sieve type synthetic zeolites is their exceedingly uniform pore sizes and volumes, which contributes "shape selectivity", which is regarded as a significant factor in the improved results obtained by this invention. The concepts of shape-selective catalysis and examples of shape-selective catalysis have been reviewed by Csicsery (J. A. Rabo, ed., *Zeolite Chemistry and Catalysis*, American Chemical Society, 1976.)

Zeolites employed in this invention must also possess stability and have effective ion-exchange capability. For example, Linde-A type zeolites are very shape-selective and have high ion-exchange capacity, but they are unstable under acidic conditions and at temperatures higher than about 550° C. On the other hand, Faujasite-type zeolites (X and Y) are less shape-selective than the type A zeolites, but can still be suitable for reactions with reactants and products which are too large to transverse the channels of the small-pore zeolite A.

Zeolite Y is acid-resistant and thermally stable up to approximately 700° C. Broadly, the upper temperature limit is approximately 800° C. In contrast, zeolites of the ZSM series, as well as Chabazite-Erionite systems have poor ion-exchange capacity due to their very large Si/Al content ratios. Mordenite zeolites also have relatively large Si/Al ratios but are still potentially desirable catalyst supports because they are as thermally stable and acid-resistant as zeolite Y and have a pore size larger than that of zeolite A but smaller than that of zeolite Y.

The following Table I presents a comparison of a number of zeolites as regards properties useful to this invention. (The last two tabulated items are naturally-occurring species, whereas the earlier-listed species are synthetic zeolites, of which the first three are particularly preferred. In general, the larger the Si/Al ratios, the poorer the ion exchange capability.) Species' properties denoted + are desirable, whereas those denoted − are not advantageous.

TABLE I

| Zeolite Type | Si/Al Ratio | Shape Selectivity | Acid Resistance Thermal Stability | Ion Exchange Capacity |
|---|---|---|---|---|
| A | ~1 | + | − | + |
| X | 1–3 | − | − | + |
| Y | >3 | − | + | + |
| Mordenite | 5 | +,− | + | +,− |
| ZSM | 6 or 6+ | +,− | + | − |
| Chabazite | 4(?) | + | + | − |

There are at least three other factors which determine catalyst composition, activity and selectivity according to this invention, including: (1) the choice of an appropriate transition metal for the conduct of the particular Fischer-Tropsch synthesis to be effected, (2) the appropriate electrochemical relationship between the transition metal preselected under (1) and an effective vaporized reducing metal and (3) the thermal stability, and acid resistance, of the synthetic zeolite support under conditions of both catalyst preparation and subsequent use.

The following Table II lists the electrochemical potentials of a number of potential transition metal, reducing metal combinations which are considered effective according to this invention, especially those denoted by a + sign. In general, the larger the reduction potential of the reductant with respect to the reduction potential of the transition metal, the better the catalytic results to be expected. However, even if the known potential of the reductant metal under the standard conditions, i.e., based on KCl half cells at 25° C., is somewhat smaller than that of the transition metal, the reductant metal may still be powerful enough to be effective under working conditions.

TABLE II

| | | | | | | |
|---|---|---|---|---|---|---|
| Reducing Metals | $Cs^+$ | + $e^-$ | $\longleftrightarrow$ | Cs | −2.923V | + |
| | $Rb^+$ | + $e^-$ | $\longleftrightarrow$ | Rb | −2.925V | + |
| | $K^+$ | + $e^-$ | $\longleftrightarrow$ | K | −2.924V | + |
| | $Na^+$ | + $e^-$ | $\longleftrightarrow$ | Na | −2.711V | + |
| | $Li^+$ | + $e^-$ | $\longleftrightarrow$ | Li | −3.045V | + |
| | $Mg^{2+}$ | + $2e^-$ | $\longleftrightarrow$ | Mg | −2.375V | + |
| | $Zn^{2+}$ | + $2e^-$ | $\longleftrightarrow$ | Zn | −0.7628V | + |
| | $Cd^{2+}$ | + $2e^-$ | $\longleftrightarrow$ | Cd | −0.4026V | + |
| | $Hg^{2+}$ | + $2e^-$ | $\longleftrightarrow$ | Hg | +0.851 | |
| Transition Metals | $Mn^{2+}$ | + $2e^-$ | $\longleftrightarrow$ | Mn | −1.029V | |
| | $Fe^{2+}$ | + $2e^-$ | $\longleftrightarrow$ | Fe | −0.409V | + |
| | $Co^{2+}$ | + $2e^-$ | $\longleftrightarrow$ | Co | −0.28V | + |
| | $Ni^{2+}$ | + $2e^-$ | $\longleftrightarrow$ | Ni | −0.23V | + |
| | $Cu^{2+}$ | + $2e^-$ | $\longleftrightarrow$ | Cu | +0.34V | + |
| | $Ag^+$ | + $e^-$ | $\longleftrightarrow$ | Ag | +0.80V | + |

TABLE II-continued

| | | | | | |
|---|---|---|---|---|---|
| $Pd^{2+}$ | + $2e^-$ | $\longleftrightarrow$ | Pd | +0.83V | + |

If a mixture of transition metal ions is employed, the mixture is appraised, vis-a-vis the reductant metal, with reference to the lowest potential transition metal involved.

It is speculated that the catalytic metal particles are distributed within the zeolite as extremely small uniform metal clusters (<10 A°) trapped within the zeolite pores. This trapping reduces migration of the catalyst through the intracrystalline channels to the outer space, or macropores, between the zeolite particles. Such migration is otherwise unavoidable, causing sintering of the metal and consequent destruction of catalytic activity and/or selectivity.

It is speculated, although confirmatory evidence has not yet evolved, that the reductant metal reduces the transition metal from the ionic state leaving it in significant amounts within the zeolite micropores, so that catalytic action is effected by the transition metal alone or by both metals individually or in concert. It appears feasible to use a mixture of transition metals, instead of only one, if this is desirable under the particular reaction circumstances. Also, if desired, a mixture of several reductants should be equally practicable. Also, it is entirely possible that reductant and transition metals combine into an alloy-like cluster. Some multivalent reductant metals, such as Cd, might remain in different reduced valent states, e.g., $Cd^{+1}$, $Cd^{+2}$ and various combinations of such species with the transition metals in situ.

Catalyst Preparation

Example 1—Catalyst Co°-CdA-CA-1-1-a

The starting zeolite was type 5A (Ca-A) marketed by Chromatography Associates, Inc., Catalog #MS560 powder. This product is a Linde-A zeolite produced by Union Carbide Corporation. It is characterized as structure Ca-A in the literature.

The zeolite was sieved at the outset and only the 60–80 mesh fraction was employed for catalyst preparation.

(a) Ion Exchange 10 g. of the starting zeolite, 5A, was placed in a 250 ml flask provided with a condenser. 100 ml of 0.1 N $CoCl_2 \cdot 6H_2O$ was added and the flask heated to ~95° C. and kept at this temperature for 2 hrs. under moderate mechanical stirring.

At this point the supernatant solution, which had lost its typical blue-purple color, was decanted and a fresh 100 ml portion of the $CoCl_2$ solution was added. The 2 hr. heating-stirring cycle was repeated, followed by decantation of left over solution. A total of six of these exchange steps were effected over a total time of 12 hrs., after which the mixture was filtered through a Büchner funnel and washed thoroughly with ion-free water until no $CL^-$ ions were detected by $AgNO_3$ test. The CoA thus obtained was then dried at 120°–140° C. for 16 hrs. This sample was designated Co-A-CA-1-1.

(b) Reduction by Metal Vapor (Cd)

Referring to FIGS. 2a, 2b and 2c, the reduction was effected as follows:

The zeolite was introduced into the pyrex main tube 10, and the Cd metal particles in 10–100 times excess (~0.5 g) Baker, Mossey, 4-1184, into pyrex side tube 11 joined to main tube 10 by a ground glass connection 12. The system was evacuated to ~$10^{-3}$ torr continuously via stopcock drawoff 15 and the main tube placed within a resistance furnace 16 which was heated gradually to 470° C. where it was maintained at this temperature for 11 hrs.

Following this stage (FIG. 2a) the zeolite powder was shaken through ground glass connection 12 from main tube 10 into side tube 11 and mixed with the Cd metal particles in bulbous end 11a. Side tube 11, still under vacuum, was sealed off and detached from the rest of the apparatus by closing off sealing point 11b in a burner flame, after which it was placed separately in resistance furnace 16 (FIG. 2b). Sealed section 11, containing the reacting mixture, was heated to 460° C. for 16 hrs., and then to 490°–500° C. for an additional period of 42 hrs., after which it was cooled to room temperature and opened. The tube contents were separated on filter paper to give cadmium metal particles and zeolite powder. The zeolite powder fraction was transferred into main tube 10, which was evacuated to ~$10^{-3}$ torr and heated in furnace 16 to 460°–500° C. for 16 hrs (FIG. 2c). Black Cd deposits were noted on the internal wall of tube 10 adjacent the entrance to furnace 16 and away from the catalyst powder. After cooling, the powder, gray-black in color, was taken out of tube 10 and stored in a vial at room temperature. This powder is designated Co°-CdA-CA-1-1-a.

Example 2—Catalyst Co°-CdY-1-1

The starting zeolite was Sk-41(HY) from the Linde Division, Union Carbide Corporation, in the form of a powder (1–2 μm particle size).

The ion exchange procedure was conducted as per Example 1, supra, thereby providing sample Co-Y-1-1.

The reduction step was essentially the same as that for Co-A supra, except that the reduction was effected as a one-step heating at 450°–460° C. for 10 hrs.

Fischer-Tropsch (F-T) Experiments-Experiment #1-FT Generally Selective Production of Propylene from (Purified) Syngas (a) 0.5063 gm of Co°-CdA-CA-1-1-a catalyst mesh size 60/80 was introduced into the reactor. The reactor was a stainless steel tube (~1 cm dia.×10 cm long) within which was placed a 1 cm×10 cm loosely rolled sheet of glass wool, (Pyrex Filtering Fiber, Corning Glass Works #3950) upon which the particulate catalyst was dusted before roll-up.

The catalyst was activated in situ by passing substantially pure $H_2$ at 1 atm. flow rate 30 cc/min., at 204° C. for 14 hrs. Afterwards, the system was cooled to ~150° C. and a mixture of substantially pure CO and $H_2$, 1:1 proportion, was flowed through the reactor at 25 cc/min. under a pressure of 92 p.s.i. with the temperature brought up to 200° C.

Chromatograms taken during the 28 hr. duration of the run showed the following:

(a) When the temperature reached 182° C., two $C_3$ products were the only ones in the gas chromatographic hydrocarbon (HC) column, these being propane (~12%) and propylene (~88%). A chromatographic column effective for determining oxygenated products appeared to indicate a product (unidentified).

After 5 hrs. at 200° C. the $C_3$ peaks decreased 3-fold and there was a slight increase in $CH_4$, which was originally present as an impurity.

(b) The reactor was cooled to room temperature then flushed with hydrogen at one atm. pressure for 4 hrs. Then a substantially pure $H_2/CO$ mixture (4% CO) was passed through the reactor under 82 p.s.i. at a rate of 30 cc/96 secs.

The temperature was raised gradually. After 20 mins., at 104° C. no HC products were detected. 35 mins. later, when the temperature had reached 153° C., there was still no HC produced. After an additional 25 minutes, at 182° C., still no HC was detected. Finally, 50 mins. later, at 217° C., propane and propylene were detected in higher yield than in (a) and at higher propane-to-propylene ratio, i.e., 1:2. A third chromatographic peak, very small, of unknown identity, existed just ahead of the propylene peak. After 50 mins. at 217°–218° C., this small peak vanished and the propane:propylene ratio changed to 2:3, respectively, and the hydrocarbon yield dropped to ~50% of the (a) yield.

After an additional period of 4 hrs., the yield dropped to ~10%, whereupon the run was continued at 235°–205° C. for an additional period of 40 hrs. with reactivity close to zero. At this point, the catalyst was reactivated for 6 hrs. by treatment with hydrogen at atmospheric pressure 30 cc/72 sec. flow rate, at ~250° C. The reactor was cooled to 135° C., followed by passing a substantially pure $CO/H_2$ mixture (4% CO) at 80 p.s.i. Gradual heating to 223° C. over a period of 2 hrs. resulted in a 2:3 propane:propylene mixture at very low yields.

The catalyst was then reactivated a second time using hydrogen at one atmosphere, 30 cc/2 min. flow rate, temperature 295° C. for 16 hrs. when the temperature was permitted to drop to ~206° C. and held at this value for an additional 16 hrs. At this point, substantially pure $CO/H_2$, (4% CO) was flowed through the reactor at 82 p.s.i., 30 cc/91 secs. flow rate and the system gradually heated up to 294° C. At the latter temperature, after 1.5 hrs., only traces of $C_3$ products were detected. The system was then cooled to 130° C. and substantially pure $CO/H_2$, 1:1 mixture, was introduced at 94 p.s.i., flow rate 30 cc/118 secs. After 1.5 hrs., at 220° C., small amounts of propylene were detected, as well as some increase in the $CH_4$ level. 1.5 hrs. later, at 223° C., the $CH_4$ increased further and became the main product, although there were some ethane and ethylene present as well as traces of propane and some propylene. After a further 30 mins. at 250° C., the same pattern existed. 30 mins. thereafter, at 275° C., the F-T spectrum became more pronounced and, finally, at 287° C., it reached a maximum, showing the Schulz-Flory distribution with $C_1$–$C_5$ product mixture. After 2.5 hrs. more at ~287° C. there was no perceptible catalyst deactivation. Estimates of the relative HC concentrations at this stage were:

TABLE III

| | $C_1$ | $C_2$ | | $C_3$ | | $C_4$ | | $C_5$ |
|---|---|---|---|---|---|---|---|---|
| | $CH_4$ | $C_2H_6$ | $C_2H_4$ | $C_2H_8$ | $C_3H_6$ | $C_4H_{10}$ | *Butenes cis-z-butene | $C_5H_{12}$ |
| Peak area | 16,468 | 3,447 | 1,274 | 1,425 | 1,727 | 375 | 280    283 | 80 |

TABLE III-continued

|  | $C_1$ | $C_2$ | | $C_3$ | | $C_4$ | | | $C_5$ |
|---|---|---|---|---|---|---|---|---|---|
|  | $CH_4$ | $C_2H_6$ | $C_2H_4$ | $C_2H_8$ | $C_3H_6$ | $C_4H_{10}$ | *Butenes | cis-z-butene | $C_5H_{12}$ |
| Corrected Intensity | 16,977 | 3,553 | 1,313 | 1,454 | 1,762 | 344 | 257 | 260 | 77 |
| Wt % | 65.3 | 13.7 | 5.0 | 5.6 | 6.8 | 1.3 | 1.0 | 1.0 | 0.3 |
| log[$HC_n$] | 0.61 | $\overline{1.66}$ | | $\overline{1.11}$ | | $\overline{2.35}$ | | | $\overline{3.62}$ |

*excluding cis-z-butene

The results are plotted as log [$HC_n$] v n, Carbon Number (FIG. 3).

At this point the heating was stopped and the system allowed to cool to room temperature overnight, still under pressure. The pressure was then released and the system purged with hydrogen for 2 hrs. at one atmosphere pressure. The catalyst was gray-black in color and showed no carbonyls in its infrared spectra.

-Experiment #2 F-T-Specific Selective Production of Propylene from (Purified) Syngas 0.5004 gm. of the same catalyst was utilized as in Experiment 1 FT. The catalyst was activated under hydrogen, one atmosphere pressure at 200° C. for 5 hrs. Then the system was cooled to ~100° C. and substantially pure $CO/H_2$ mixture, 1:1 proportions, was flowed through under 95 p.s.i. The system was heated gradually to 100° C. After one hour at 126°-8° C., only traces of propylene were detected. After ~30 mins. at 151° C., the concentration of propylene, as the only HC product, started to build up, reaching its highest level after ~2 hrs., and remaining constant for 18 hrs. This is shown in FIG. 4.

-Experiment #3 F-T-Unreduced Co Not Effective 0.500 gm. of Co-A-CA-1-1, 60/80 mesh was employed as catalyst. The reactor was first flushed with substantially pure hydrogen at one atmosphere pressure, 30 cc/130 sec. flow rate, heated to 200° C. The catalyst was activated at this temperature for 5 hrs., followed by cooling to ~100° C.

Substantially pure $CO/H_2$, 1:1 mixture, was introduced at 93 p.s.i. and the temperature raised to 150° C. No reaction was detected, as shown by the HC chromotograph column after 1.5 hrs. at this temperature. The temperature was then raised to 185° C. and kept at this temperature for one hour during which only traces of propylene were detected. The blue catalyst powder recovered after the run showed no CO peak in the infra-red spectrum.

-Experiment #4 F-T-Selective Production of $C_4$–$C_6$ Products Primarily 0.4907 gm. of Co°-CdY-1-1 was the catalyst, activated by flushing with substantially pure hydrogen (1 atm. pressure) at 200° C. for 9.5 hrs. at 30 cc/104 sec. flow rate.

After cooling to 65° C., substantially pure $CO/H_2$, 1:1 proportions, was introduced and passed through the reactor at 95 p.s.i., flow rate 30 cc/110 secs.

At 103° C. no HC products were formed but, on the oxygenated products chromatograph, the single peak detected in Experiment #2 F-T appeared again.

After 4 hrs. at 103° C. the temperature was raised to 152° C. The first chromatogram at this temperature showed the production of $CH_4$ and traces of higher HC products (i.e., $C_2$–$C_4$). The oxygenated products chromatographic column again showed the presence of the undetermined peak of Experiment #2 F-T (a).

After 5.5 hrs. at 153° C., the product concentrations were slightly higher, but the pattern remained the same. At this point, the temperature was raised to 182° C. and a "full F-T spectrum" resulted. This spectrum was as follows:

TABLE IV

|  | $C_1$ | $C_2$ | | $C_3$ | | $C_4$ | | |
|---|---|---|---|---|---|---|---|---|
|  | $CH_4$ | $C_2H_6$ | $C_2H_4$ | $C_3H_8$ | $C_3H_6$ | n-$C_4H_{10}$ | i-$C_4H_{10}$ | $C_4H_8$ |
| Peak area | 43,733 | 4,209 | 1,066 | 5,228 | 2,524 | 55,611 | 2,530 | 700 |
| Corrected Intensity | 45,085 | 4,332 | 1,099 | 5,335 | 2,575 | 51,019 | 2,321 | 640 |
| Wt % | 25.0 | 2.4 | 0.6 | 3.0 | 1.4 | 28.3 | 1.3 | 0.3 |
| log[$HC_n$] | 0.19 | $\overline{2.90}$ | | $\overline{2.83}$ | | $\overline{1.69}$ | | |

|  | $C_5$ | | | $C_6$ | | | |
|---|---|---|---|---|---|---|---|
|  | n-$C_5H_{12}$ | i-$C_5H_{12}$ | $C_5H_{10}$ | n-$C_6H_{14}$ | i-$C_6H_{14}$ | $C_6H_{12}$ | $C_7H_{16}$ |
| Peak area | 37,218 | 1,300 | 2,000 | 16,760 | 1,000 | 6,000 | 5,000 |
| Corrected Intensity | 35,786 | 1,250 | 1,920 | 16,270 | 970 | 5,800 | 5,000 |
| Wt % | 19.9 | 0.7 | 1.1 | 9.0 | 0.5 | 3.2 | 2.8 |
| log[$HC_n$] | $\overline{1.44}$ | | | $\overline{1.02}$ | | | $\overline{2.45}$ |

FIG. 3 presents the comparison of the Table IV analyses as a Schulz-Flory plot for both the A- and the Y-based catalysts.

After 2 hrs. at 182°-3° C. there was no sign of deactivation of the catalyst. 3.5 hrs. after the catalyst temperature reached 182° C., heating was stopped and the system was cooled under pressure. Approximately 6 hrs. later the catalyst was removed from the reactor. The color was gray and the catalyst displayed no carbonyl peak in the infrared spectrum.

TABLE V

Summary of Experiments #1-4 F-T

| Exp. | Catalyst | Step | Activation (under $H_2$) flow, 1 atm) | Reaction Conditions Temp. °C. | Total Pressure, Psi | $CO:H_2$ Ratio | Detectable HC Product Mixture | Remarks |
|---|---|---|---|---|---|---|---|---|
| 1-F-T | Co°-CdA | (1) | 204° C., 14hr | 182-200 | 92 | 1:1 | propane, ~12% propylene, ~88% | fast deactivation accompanied by formation of some $CH_4$ |
| | | (2) | 25° C., 4 hr | 217 | 82 | 1:24 | propane, 30-40% propylene, ~60% undetected product, 10-0% | fast deactivation, higher conversion |
| | | (3) | 250° C., 6hr | 223 | 80 | 1:24 | propane, 40% propylene, 60% | lower conversion |
| | | (4) | 295° C., 16hr | 294 | 82 | 1:24 | traces $C_3$ | |
| | | (5) | — | 220-250 | 94 | 1:1 | mainly $CH_4$ traces $C_2$, $C_3$ | |
| | | | | 287 | | | $C_1$-$C_5$ (see FIG. 5) | higher conversion |
| 2-F-T | Co°-CdA | | 200° C., 5hr | 151 | 95 | 1:1 | propylene, 100% | no deactivation during 17.5 hr. |
| 3-F-T | Co-A | | 200° C., 5hr | 150 | 93 | 1:1 | — | |
| | | | | 185 | | | traces of propylene | |
| 4-F-T | Co°-CdY | | 200° C., 9.5hr | 152 | 95 | 1:1 | mainly $CH_4$ | slightly higher conversion after 5.5hr |
| | | | | | | | traces $C_2$-$C_4$ | |
| | | | | 182 | | | mainly $CH_4$ and $C_4$-$C_6$ (see FIG. 5) | |

It will be understood that, in the catalyst preparation, drying, after incorporation of the transition metal, can be achieved in a variety of ways, so long as superfluous reductant metal, by which is meant all reductant metal not incorporated in the zeolite, or retained within the zeolite channels, is removed.

It is believed that our catalyst will function under the same pressure and temperature limitations as conventional Fischer-Tropsch catalyst, i.e., above about one atmosphere pressure and below about 400° C.

What is claimed is:

1. A Fischer-Tropsch type catalyst comprising a particulate synthetic zeolite catalyst support having a pore size in the range of 2-10 Å, which has ion exchange properties, within which there is incorporated, by ion exchange, at least one reducible transition metal having catalytic properties effective in the conversion of CO and $H_2$ to hydrocarbon products consisting essentially of cobalt, said transition metal being reduced by the vapor of at least one preselected reductant metal consisting essentially of cadmium having a reduction potential greater than the reduction potential of said transition metal at a temperature below about 800° C.

2. The method of preparing a Fischer-Tropsch catalyst comprising in sequence: (a) contacting a particulate synthetic zeolite catalyst support having a pore size in the range of 2-10 Å with a solution of a salt of a reducible transition metal having catalytic properties effective in the conversion of CO and $H_2$ to hydrocarbon products consisting essentially of cobalt; (b) drying to eliminate substantially all water from the zeolite pores; (c) reducing a substantial proportion of the transition metal within the dried reducible transition metal solution-treated zeolite prepared per step (b) by exposure to the vapor of a reductant metal consisting essentially of cadmium, having a reduction potential greater than the reduction potential of said transition metal at a temperature below about 800° C.; (d) heating the product of step (c) to remove superfluous reductant metal from said product of step (c); and (e) cooling under vacuum or in an inert atmosphere to a temperature below about 200° C.

3. A Fischer-Tropsch catalyst according to claim 1 wherein said particulate synthetic zeolite catalyst support is one of the group consisting of types A, X and Y.

* * * * *

UNITED STATES PATENT AND TRADEMARK OFFICE
CERTIFICATE OF CORRECTION

PATENT NO. : 4,294,725
DATED : October 13, 1981
INVENTOR(S) : Dan Fraenkel and Bruce C. Gates It is certified that error appears in the above—identified patent and that said Letters Patent is hereby corrected as shown below:

Col. 1, line 23, "catalyst" should read -- catalysts --.

Col. 1, line 52. "selectively" should read --selectivity--

Col 2, line 6. The word -the- should follow "from"

Col. 2, line 39. The zero should be deleted from the space enclosed by the brackets [ ]

Col. 4, line 62. "CL$^-$" should read --Cl$^-$--

Col. 5, line 3. "Mossey" should read --Mossy--

Signed and Sealed this

Fifth Day of January 1982

[SEAL]

Attest:

Attesting Officer

GERALD J. MOSSINGHOFF

Commissioner of Patents and Trademarks